United States Patent
Sievers et al.

(10) Patent No.: US 10,610,352 B2
(45) Date of Patent: Apr. 7, 2020

(54) HEART VALVE PROSTHESIS

(71) Applicant: Hans-Hinrich Sievers, Kronshagen (DE)

(72) Inventors: Hans-Hinrich Sievers, Kronshagen (DE); Michael Scharfschwerdt, Lübeck (DE); Andreas Hof, Lübeck (DE)

(73) Assignee: SIEVERS, HANS-HINRICH, DR., Kronshagen (DE)

( * ) Notice: Subject to any disclaimer, the term of this patent is extended or adjusted under 35 U.S.C. 154(b) by 90 days.

(21) Appl. No.: 15/523,745

(22) PCT Filed: Nov. 16, 2015

(86) PCT No.: PCT/DE2015/200502
§ 371 (c)(1),
(2) Date: May 2, 2017

(87) PCT Pub. No.: WO2016/078659
PCT Pub. Date: May 26, 2016

(65) Prior Publication Data
US 2017/0312073 A1    Nov. 2, 2017

(30) Foreign Application Priority Data

Nov. 18, 2014   (DE) .................. 10 2014 223 522

(51) Int. Cl.
*A61F 2/24* (2006.01)
(52) U.S. Cl.
CPC .......... *A61F 2/2409* (2013.01); *A61F 2/2412* (2013.01); *A61F 2/2418* (2013.01); *A61F 2210/0014* (2013.01); *A61F 2220/0008* (2013.01); *A61F 2220/0033* (2013.01); *A61F 2230/0054* (2013.01); *A61F 2230/0069* (2013.01); *A61F 2250/0018* (2013.01)

(58) Field of Classification Search
USPC ..................................................... 623/1.1–3.1
See application file for complete search history.

(56) References Cited

U.S. PATENT DOCUMENTS

| | | | |
|---|---|---|---|
| 6,350,282 B1* | 2/2002 | Eberhardt ............. | A61F 2/2409 623/2.13 |
| 6,736,845 B2* | 5/2004 | Marquez ............... | A61F 2/2412 623/2.11 |
| 7,252,681 B2* | 8/2007 | Berg ..................... | A61F 2/2412 623/2.14 |
| 7,513,909 B2* | 4/2009 | Lane ..................... | A61F 2/2409 623/2.4 |

(Continued)

FOREIGN PATENT DOCUMENTS

| | | |
|---|---|---|
| DE | 10 2010 051 632 B4 | 9/2013 |
| WO | 95/28899 A1 | 11/1995 |
| WO | 03/068108 A1 | 8/2003 |

*Primary Examiner* — Yashita Sharma
(74) *Attorney, Agent, or Firm* — McGlew and Tuttle, P.C.

(57) ABSTRACT

A heart valve prosthesis includes a valve frame (2), on which frame several valve leaflets (8) are fastened, as well as a fastening region which connects axially onto the valve frame (2), for fastening in a blood vessel. The fastening region includes a stabilizing ring (14, 14', 14", 14''', 14'''') which defines a given shape and a given diameter and is connected to the valve frame (2) is a force-decoupled manner.

18 Claims, 8 Drawing Sheets

(56) References Cited

U.S. PATENT DOCUMENTS

| 9,414,913 B2* | 8/2016 | Beith | A61F 2/2418 |
| 2014/0371842 A1* | 12/2014 | Marquez | A61F 2/2445 |
| | | | 623/2.11 |

* cited by examiner

HEART VALVE PROSTHESIS

CROSS REFERENCE TO RELATED APPLICATIONS

This application is a U.S. National Phase Application of International Application PCT/DE2015/200502, filed Nov. 16, 2015, and claims the benefit of priority under 35 U.S.C. § 119 of German Application 10 2014 223 522.7, filed Nov. 18, 2014, the entire contents of which are incorporated herein by reference.

FIELD OF THE INVENTION

The invention relates to a heart valve prosthesis with a valve frame, on which frame several valve leaflets are fastened, as well as with a fastening region which connects axially onto the valve frame, for fastening in a blood vessel.

BACKGROUND OF THE INVENTION

A biological heart valve prosthesis which comprises a valve frame, on which several semilunar valves of biological material are fastened, is known for example from DE 10 2010 051 632 B4. A suture ring of a fabric material is arranged on the axial end of the valve frame, in order to be able to suture the heart valve prosthesis into the aorta. On inserting such heart valve prostheses, it is a problem to find a heart valve prosthesis in a size matching the respective patient, in order for it to be able to be inserted into the aorta, where possible, without a narrowing of the flow cross section.

SUMMARY OF THE INVENTION

Against this background of the state of the art, it is an object of the invention to provide a heart valve prosthesis which can be simply inserted into a blood vessel and thereby reliably ensures the desired flow cross section.

With regard to the heart valve prosthesis according to the invention, it is particularly the case of an aorta valve prosthesis.

The heart valve prosthesis according to the invention comprises a valve frame, on which several valve leaflets or semilunar valves, preferably three valve leaflets as is generally known, are fastened. The valve frame preferably consists of a bent metallic wire which is shaped such that three arches are formed, said arches with their ends being adjacent one another and being connected to one another via smaller connecting arches. These connecting arches form commissures between the valve leaflets, said commissures being fastened in the arches. The connecting arches, which is to say the tips of the commissures, form a first, in particular downstream axial end of the heart valve prosthesis. A fastening region which connects axially onto the valve frame and which is designed for fastening, in particular of suturing (stitching) in a blood vessel, e.g. the aorta, is located at the opposite, second axial end of the heart valve prosthesis. A suture ring which is formed from an elastic material or from a fabric or textile and through which the heart valve prosthesis can be sutured to the surrounding vessel can be arranged in this region for example.

According to the invention, a stabilizing ring is arranged in the fastening region. This stabilizing ring has a predefined shape, in particular a shape with circular cross section. The stabilizing ring thus defines a predefined diameter of the fastening region and according to the invention is connected to the valve frame in a decoupled manner with regard to force. This means that the connection between the stabilizing ring and the valve frame is designed elastically which is to say in a movable manner, so that forces acting upon the stabilizing ring are not or essentially not transmitted onto the valve frame and vice versa. Thus in particular a flexible connection can be present between the stabilizing ring and the valve frame, wherein this connection ensures a certain movability and force decoupling. The force-decoupled connection between the stabilizing ring and the valve frame has the advantage that the forces acting upon the fastening region are not transmitted onto the valve frame, so that the valve frame is not deformed by the fastening and not subjected to force, so that the functionality of the valve leaflets is not compromised. This permits the heart valve prosthesis to be inserted into a vessel significantly more tautly and in an accurately fitting manner, since certain forces can be exerted onto the surrounding tissue by the stabilizing ring and, as the case may be, a certain widening (expansion) of the surrounding tissue can also be achieved. It therefore becomes possible to insert a maximally large heart valve prosthesis into the vessel, so that the flow cross section is not significantly restricted compared to the natural cross section. However, it is simultaneously ensured that an undesirable deformation or compromising of the movement of the valve frame and of the valve leaflets does not occur with this accurately fitting, taut insertion of the heart valve prosthesis.

The valve leaflets are preferably manufactured of biological material. The valve leaflets can be connected to the valve frame in the known manner, for example by way of suturing. The valve frame in the known manner is thereby preferably surrounded by a sheath, in particular of a textile or fabric material, in the known manner. The sheath thereby in particular closes the region of the commissures between the arches of the valve frame which carry the valve leaflets, said commissures having been described above.

The valve frame is preferably designed in an elastically deformable manner. The movability of the valve leaflets is therefore improved. The valve frame can moreover be elastically deformable, in particular elastically deformable in the radial direction, in a manner such that it can be reduced in its cross section or diameter, for inserting the heart valve prosthesis into vessel, and can expand after the insertion, so that after the insertion it can widen in its diameter into the Sinus aortae. In particular, the valve frame can be elastically deformed in the radial direction before the insertion, in order to reduce the outer cross section. On insertion, the valve frame can be held in this deformed position by way of suitable holding means and then be deformed elastically back into the relaxed initial shape after the insertion, by way of releasing the holding means. Thereby, the valve frame can then expand or widen in the radial direction. The valve frame in the relaxed condition preferably has a larger outer cross section than the stabilizing ring. The valve frame can thus expand into the Sinus aortae. A large as possible flow cross section can therefore be ensured. Such a design is known for example from DE 10 2010 051 632 B4, which is referred to here.

The stabilizing ring is particularly preferably connected to the valve frame via a textile or fabric material, wherein the textile material or fabric material preferably envelops the valve frame and/or the stabilizing ring. Such a textile or fabric material creates the sufficiently movable connection between the valve frame and the stabilizing ring, so that a force decoupling is given. The textile or fabric material can moreover be simultaneously used to suture (stitch) the heart valve prosthesis to the surrounding blood vessel, into which vessel the heart valve prosthesis is inserted.

Particularly preferably, the stabilizing ring at least in the radial direction has a lower elastic deformability than the valve frame and is preferably designed in an essentially rigid manner. If the stabilizing ring has a lower elastic deformability in the radial direction than the valve frame, then it can preferably be seen as being rigid relative to the valve frame. Whereas the valve frame is deformable, in order after the insertion for example to expand as described above and to ensure the necessary movability of the valve leaflets, the stabilizing ring is preferably rigid to the extent that after insertion, it is no longer significantly deformed by the surrounding vessel, but in contrast is particularly preferably in the position of stretching or expanding the surrounding vessel to the diameter set by the stabilizing ring. A defined cross section, which is to say flow cross section of the heart valve prosthesis, is therefore ensured by the stabilizing ring.

The stabilizing ring is preferably manufactured of metal, which is to say in particular of a biocompatible material. Particularly preferably, the stabilizing ring can be manufactured of a shape memory alloy such as nitinol. Such a design from shape memory alloy has the advantage that the stabilizing ring can be deformed, in particular reduced in its diameter, before the insertion into the vessel, so as to simply this insertion. The stabilizing ring, by way of temperature change can subsequently be expanded again into its initial, defined shape, in which it assumes the stabilizing function described above. Once it has assumed the predefined shape again, it is preferably sufficiently rigid, which is to say has so little elasticity in the aforementioned manner that it is not or not significantly deformed by the surrounding tissue of the vessel and thus ensures a defined cross section.

According to a particular embodiment of the invention, the stabilizing ring can comprise commissure supports which project in the axial direction, are fixedly connected to the stabilizing ring and as projections extend into the commissures formed by the valve frame. This means that the projections extend into the region between the arches of the valve frame which have been described above and which serve for supporting the commissures and in particular the material closing the commissures, in particular textile or fabric material, so that a restriction of the flow cross section by way of this material or this sheathing of the valve frame does not occur in the region of the commissures. A defined shape of the commissures can therefore be ensured by way of the firm projections, even with an elastic deformability of the valve frame.

Further preferably, the stabilizing ring has an inner cross section which corresponds to the inner cross section delimited by the commissures of the valve frame. The inner cross section of the heart valve prosthesis is thus preferably defined by the stabilizing ring together with the commissures.

The stabilizing ring further preferably has an inner cross section which corresponds to the cross section of the natural blood vessel, in particular of the aorta, for which the heart valve prosthesis is dimensioned. This means that a heart valve prosthesis which matches the blood vessel and which has a stabilizing ring whose inner cross section corresponds to the diameter or cross section of the natural blood vessel is selected on insertion. As described, the blood vessel can be widened or expanded by a certain amount on insertion, so that after the insertion of the heart valve prosthesis, its inner cross section, in particular the inner cross section in the region of the stabilizing ring, corresponds to the natural inner cross section of the blood vessel, so that a narrowing of the flow path does not occur.

According to a particular embodiment of the invention, the stabilizing ring at its outer periphery can be provided with projections, which is to say in particular radially outwardly directed projections which are provided for engaging into surrounding tissue, i.e. body tissue and in particular are designed in the form of a thread. These projections serve for the fixation of the stabilizing ring in the blood vessel. This fixation can be used additionally to a suturing or particularly preferably, alternatively to a suturing. A sutureless fastening thus becomes possible. If the projections are designed in the form of one or more thread flights, or individual projections are arranged such that together they define a thread shape, then it becomes possible to screw the heart valve prosthesis with the stabilizing ring into the blood vessel. Projections which form undercuts or are designed in the form of barbs are particularly preferably, so that a secure fixation secured again detaching is achieved. The projections or protrusions engage into the tissue and hold or fix the stabilizing ring and thus the complete heart valve prosthesis.

The arrangements of projections or protrusions for engaging into the surrounding tissue are not limited to the previously described heart valve prosthesis claimed in this application and in particular are not limited to a biological heart valve prosthesis. Such a design can be applied to any heart valve prosthesis. E.g. a mechanical heart valve prosthesis can be provided with a fastening ring or stabilizing ring with projections, which is designed in such a manner. The subject-matter of this application is therefore also a heart valve prosthesis which comprises a fastening ring which on its outer periphery is provided with projections or protrusions which are provided for engaging into surrounding tissue and in particular are designed in the form of a thread. Such a fastening ring with regard to its fastening would correspond to the stabilizing ring which is described above and hereinafter.

According to a further preferred embodiment, the projections are deformable or are designed from a shape memory material such as nitinol. This permits the projections to change in their alignment, at least between two positions. Thus for inserting the heart valve prostheses, the projections can be situated in a first position, in which they do not project radially outwards, so that the heart valve prosthesis can be inserted into the tissue without damage to this. In a second position, the projections can then be directed such that they are directed radially outwards and engage into the tissue and thus secure the heart valve prosthesis in the tissue. Thereby, it is to be understood that as the case may be, also only a part of the projections or sections of the projections can be movable or deformable between a first position and a second position in this manner. For example, sections or individual projections can be arranged such that in their second position they form barbs and in their first position they are situated such that they do not inhibit an insertion of the heart valve prosthesis, in particular a screwing-in. The movement or deformation between the first and the second position can be effected for example by way of heating for example in the case of the use of a shape memory material. However, other methods for deformation are also possible, for example also the expansion with the help of a balloon, by way of which the projections are pressed outwards into their second position.

According to a further preferred embodiment, the projections on the stabilizing ring or fastening ring in the region of the commissures or the interleaflet triangles are free of projections. These are those regions of the heart valve prosthesis which in the inserted condition of the heart valve prosthesis lie oppose the mentioned interleaflet triangles. By way of this, one prevents the projections from injuring the surrounding tissue and in particular the nerves which are situated there, in these regions. In particular, these are the regions, at which the commissures supports of the heart valve prosthesis as have been described above are situated.

According to a further embodiment of the invention, the stabilizing ring can be provided with radial openings, in particular radially extending through-holes. These on the one hand can serve for leading threads for suturing, through the stabilizing ring. On the other hand, the openings can also serve for the tissue of the blood vessel being able to penetrate into these openings, and thus contributing to the fixation of the stabilizing ring in the blood vessel.

Further preferably, the heart valve prosthesis according to the invention can comprise a flexible suture ring in the fastening region, with which suture ring the heart valve prosthesis can be sutured in the blood vessel. Here, a flexible suture ring which overlaps the stabilizing ring in its outer periphery at least in sections is particularly preferably provided. This permits the tissue of the blood vessel, to which tissue the heart valve prosthesis is to be sutured, to be arranged between this flexible suture ring and the stabilizing ring and to be sutured through the stabilizing ring and the flexible suture ring. Alternatively, a second suture ring which is overlapped by the suture ring overlapping on the outer periphery can be provided in the fastening region, on the stabilizing ring, so that the tissue can be fixed and sutured between two suture rings. With this embodiment, one can make do without the felts which are otherwise common on suturing, since the tissue can thus be fixed between two suture rings or between the stabilizing ring and the suture ring, wherein the suture rings and, as the case may be the stabilizing ring serve as counter surfaces for the threads used on suturing.

According to the invention, the stabilizing ring with the valve frame and the valve leaflets form a premanufactured construction unit which is envisaged to be inserted as a whole into a blood vessel. This means that it is not necessary to create a connection between the stabilizing ring and the valve frame on or after the insertion.

According to a further preferred embodiment of the invention, which can also be realized independently of the above described designs/embodiments, the heart valve prosthesis comprises a valve frame with several, preferably three valve leaflets. These valve leaflets are preferably manufactured of biological material. The valve leaflets according to this preferred embodiment have such a shape that in the opened condition of the heart valve prosthesis, they define sections of the peripheral surface of a cylinder, in particular of a circular cylinder. The valve leaflets in the opened condition, together with the commissures formed by the valve frame span an essentially circularly cylindrical peripheral surface which permits a maximal possible flow cross section.

In order to render this possible, the valve leaflets are preferably shaped such that they describe the shape of a circular arc at each axial position between two oppositely lying linking points onto the valve frame, wherein all arcs have the same radius of curvature. This means that the connecting lines of two opposite points on an arch of the valve frame and which run from the from the valve leaflet in the peripheral direction have the shape of an arc, wherein these arcs have the same radius of curvature at each axial position of the valve leaflet. It is therefore ensured that the valve leaflets can open to such an extent that they commonly span essentially the contour of a circular cylinder and thus release a maximal flow cross section.

This shape of the valve leaflets is particularly preferably achieved by a special shape of the outer contour of the valve leaflet which is adjacent to the valve frame. Each valve leaflet firstly basically has two regions of the outer contour. A first region forms the free face edges or contact edges of the valve leaflet which come to sealingly bear on the face edges of the other valve leaflets in the closed condition. A second region is adjacent an arch of the valve frame and is connected to the valve frame there. This region of the outer contour which is adjacent to the valve frame which is to say is fastened to an arch of the valve frame, has a shape or contour which is composed essentially of at least three, preferably five arcs which is to say sections of circles. The contour firstly comprises to outer arcs on sides which are opposed to one another, said arcs preferably having the same radius of curvature and being curved to the outside. This means that the middle points, about which these arcs are curved, lie outside the outer contour of the valve leaflet. These outer circular arcs are adjacent to the free face edges which come to sealing bear on the free face edges of the other valve leaflets. At least one inner arc which is inwardly curved is situated between these two outer arcs. This means that the middle point, about which this arc is curved, lies in the inside of the outer contour of the valve leaflet which is to say of the surface spanned by this outer contour. Particularly preferably, three inner arcs are provided, wherein a middle one of the inner arcs has a larger radius of curvature than the two arcs which are situated laterally of the middle, inner arc and which for their part are adjacent the outer arcs. These two inner arcs which are adjacent the outer arcs preferably have the same radius of curvature, but are arcuate which is to say curved about different points. As a whole, the outer contour of the valve leaflet which is adjacent the valve frame when the valve leaflet is spread out in a flat manner, thus has an essentially U-shaped shape, wherein the free ends of the limbs of this U are actuate to the outside, which is to say away from one another.

It is to be understood that the described special shaping of the valve leaflets can be realized independently of the use of a stabilizing ring or fastening ring, as has been described above. Inasmuch as this is concerned, the inventive design of the shape of the valve leaflets is not limited to the combination with these features.

The invention is hereinafter described by way of example and by way of the accompanying figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
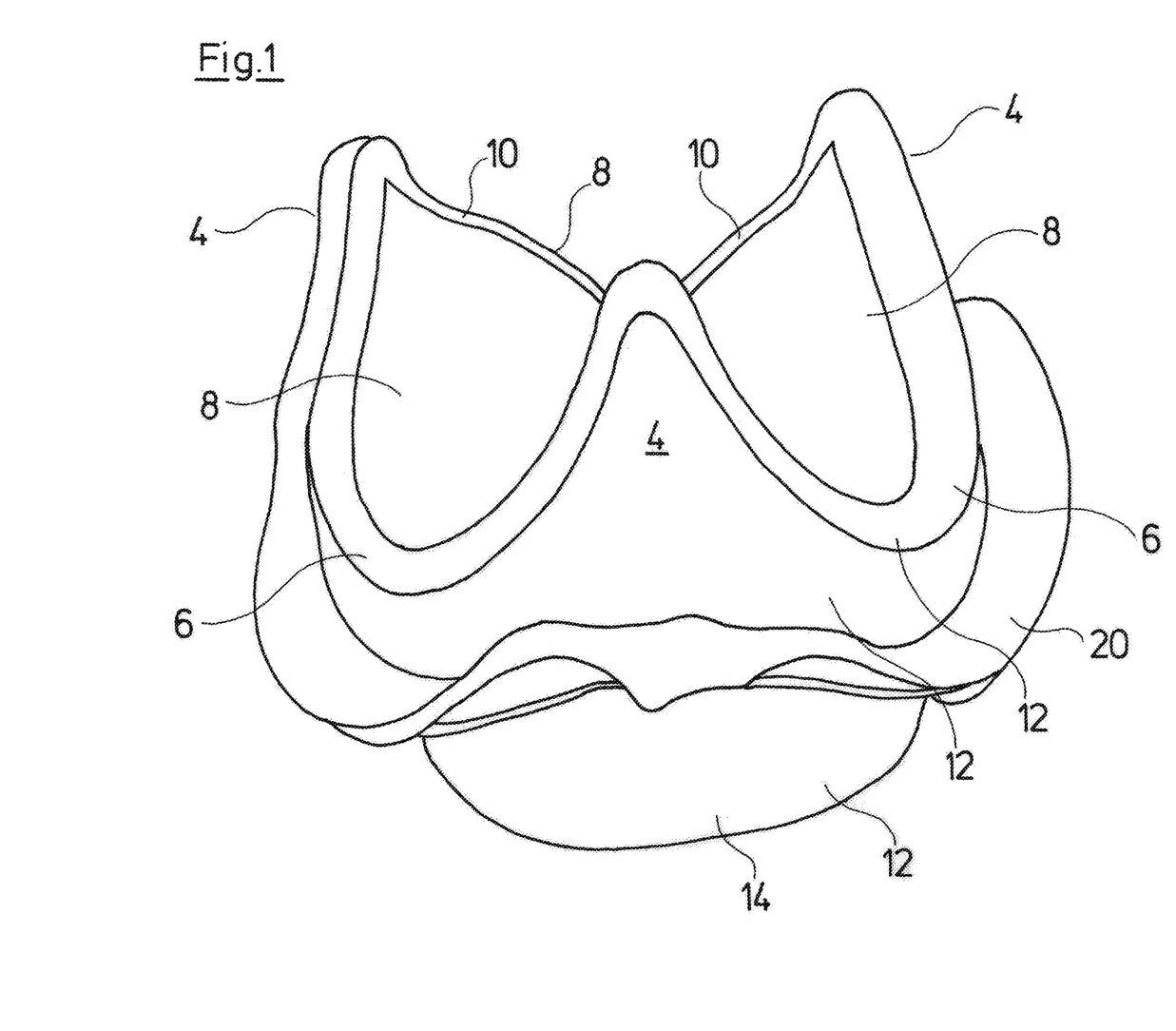
FIG. 1 is a perspective view of a heart valve prosthesis according to the invention.
Figure 2:
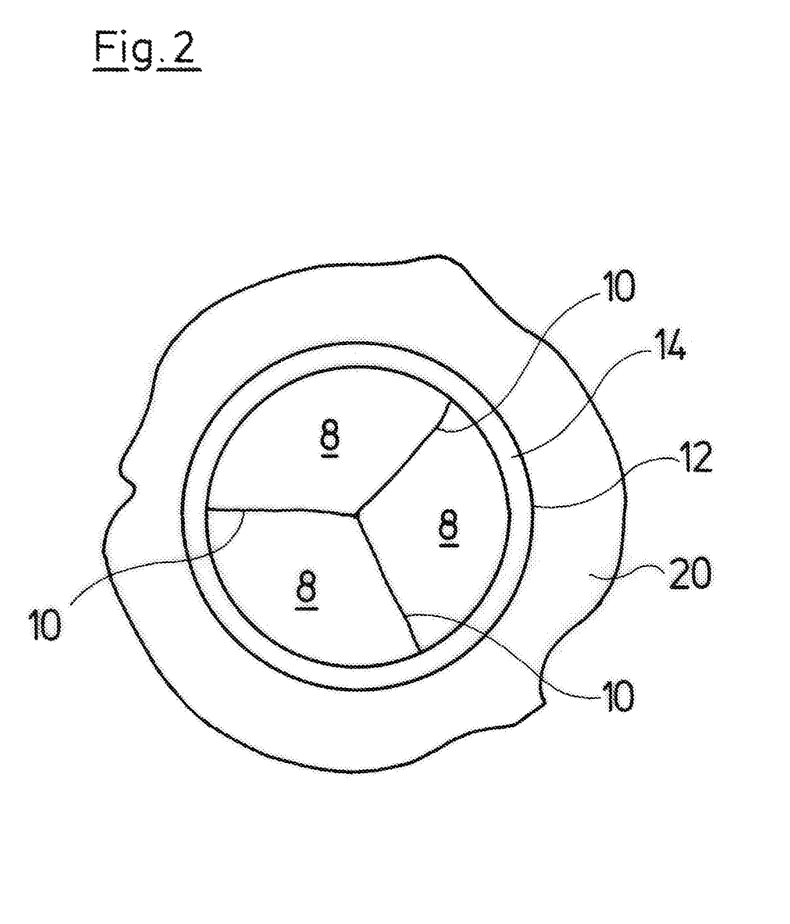
FIG. 2 is a plan view of the heart valve prosthesis according to FIG. 1, from below.
Figure 3:
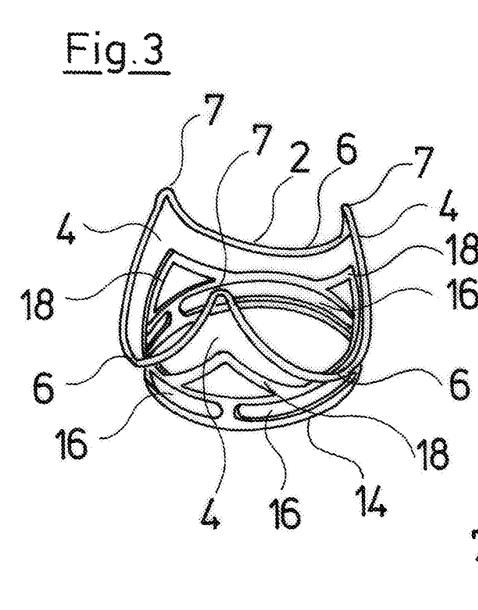
FIG. 3 is a perspective view of the valve frame and of the stabilizing ring of the heart valve prosthesis according to FIGS. 1 and 2.
Figure 4:
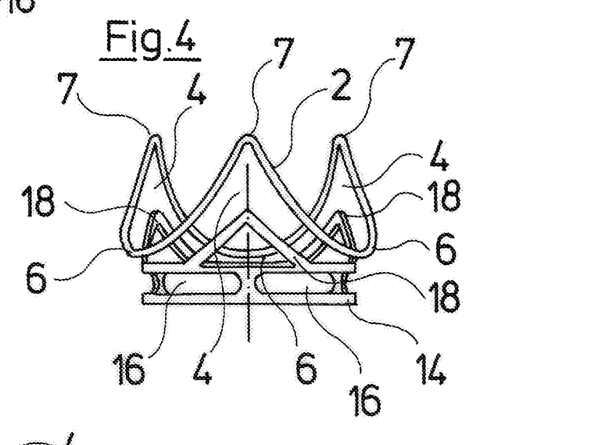
FIG. 4 is a lateral view of the valve frame and of the stabilizing ring according to FIG. 3.
Figure 5:
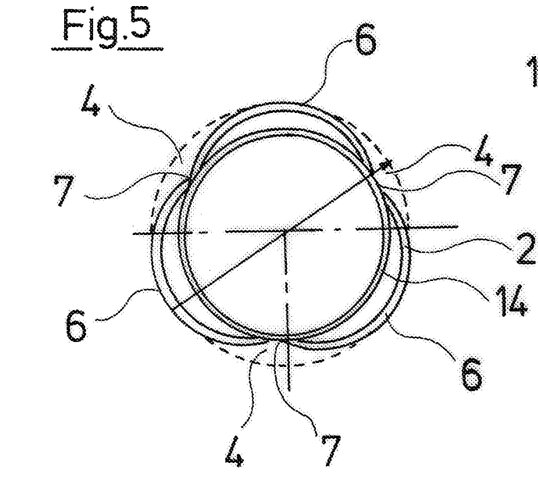
FIG. 5 is a plan view of the arrangement of the valve frame and of the stabilizing ring according to FIG. 4, from above.

Referring to the drawings, the heart valve prosthesis according to the invention, which is shown in FIGS. 1 and 2, in its inside, as is shown in FIGS. 3 to 5, comprises a valve frame 2 having three arches 6 which at their ends are connected to one another by way of connecting arches 7 and thus form three commissures 4. The valve frame 2 is formed from a metallic wire which is elastically deformable. The three arches 6 carry three valve leaflets 8 of biological material. These semilunar valves or valve leaflets 8 abut on another at three contact edges 10 and are sealed to one another there. For opening, the valve leaflets 8 move radially outwards, so that they disengage at the contact edges 10 and release a central opening.

The valve frame 2 is otherwise enveloped by a sheath 12 of a textile or fabric material which also extends over the commissures 4 and peripherally closes these. A first downstream axial end of the heart valve prosthesis is defined by the tips or connecting arches 7 of the commissures 4. A fastening region is formed at the opposite, upstream axial end. There, a stabilizing ring 14 is located in the inside of the sheath 12. The stabilizing ring 14 is manufactured of metal and comprises a defined annulus shape. The inner cross section of the stabilizing ring 14 corresponds essentially to the inner cross section between the tips of the commissures 14 and defines the maximal flow cross section through the heart valve prosthesis. This can be recognized particularly well from FIG. 5.

The stabilizing ring 14 is designed rigidly compared to the valve frame 2, which is to say it has a lower elasticity or deformability than the valve frame 2. In particular, the stabilizing ring 14 is essentially not elastically deformable in the radial direction. The stabilizing ring 14 comprises openings 16 in the radial direction. These openings 16 permit suture material which is to say threads to be led through the stabilizing ring 14, in order to fasten the heart valve prosthesis on the stabilizing ring 14 in a blood vessel. The stabilizing ring 14 at an axial end moreover comprises three commissure supports 18 which extend into the commissures 4 of the valve frame 2. These commissure supports 18 support the sheath 12 in the region of the commissures 4, so that these are held in a defined shape.

The valve frame 2 and the stabilizing ring 14 are not directly connected to one another, as can be recognized in FIGS. 3 and 4, which represent the arrangement of the valve frame 2 and of the stabilizing ring 14 in the inside of the heart valve prosthesis shown in FIG. 1. In contrast, the valve frame 2 and the stabilizing ring 14 are connected to one another solely by way of a flexible sheath 12 of textile or fabric material, so that a force-decoupled connection between the valve frame 2 and the stabilizing ring 14 is given. The valve frame 2 can move relative to the stabilizing ring 14 on account of the flexibility of the fabric material of the sheath 12. This permits an elastic deformability of the valve frame 2, in particular in the radial direction, whereas the stabilizing ring 14 is not deformed due to its rigid design. Despite this, the stabilizing ring 14 and the valve frame 2 with the valve leaflets 8 formed therein, by means of the sheath 12 form a premanufactured construction unit which in its entirely can be inserted into a blood vessel, without assembly activities or a suturing between the stabilizing ring 14 and the valve frame 2 with the valve leaflet 8 yet becoming necessary on operation.

FIGS. 3 to 5 show the non-deformed, relaxed condition of the valve frame 2. It can be recognized that in this condition, the arches 6 of the valve frame 2 comprise a plurality of lower arcuate portions that extend radially beyond the outer periphery of the stabilizing ring 14, whereas the commissures 4 are situated essentially on the periphery of the stabilizing ring 14. The arches 6 of the valve frame 2 can therefore extend into the Sinus aortae in the implanted condition and thus release a maximal inner cross section which corresponds essentially to the natural cross section of the aorta. For this, the shown heart valve prosthesis with regard to its dimensioning is matched to the respective blood vessel, so that the inner diameter of the stabilizing ring 14 corresponds essentially to the natural inner diameter of the aorta or is slightly larger. A certain expansion or widening of the tissue of the blood vessel can thus be achieved on insertion, so that as a whole, the flow cross section through this heart valve prosthesis is not restricted.

As is known from DE 10 2010 051 622 B4, the valve frame 2 can be moved radially inwards, so that the arches 6 are deformed radially inwards and the maximum outer diameter is defined by the stabilizing ring 14, for insertion. The suturing is therefore simplified. This deformation of the valve frame 2 can be released after the suturing, so that the arches 6 then expand again on account of their elasticity, as described beforehand, and in particular can expand into the Sinus aortae. This is particularly possible on account of the flexible, force-decoupled connection of the valve frame 2 to the stabilizing ring 14. The stabilizing ring 14 is designed in an adequately rigid manner, in order to define the inner cross section of the heart valve prosthesis and for this to be firmly inserted into the blood vessel, which is to say into the aorta and to be fixed there. Thereby, the stabilizing ring 14 specifies a defined size and shape of the heart valve prosthesis and in particular of its flow cross section.

The stabilizing ring 14 can be manufactured of a shape memory alloy, such as nitinol, so that it is possible to radially deform it before the insertion, so that its outer cross section is reduced. After the insertion, it can then move back into the shown initial shape by way of a change in temperature, and then be firmly fixed in a blood vessel, where, as a rigid structure, it then defines the desired cross section.

A suture ring 20 of textile or fabric material which overlaps the stabilizing ring 14 at the outer periphery is moreover arranged on the sheath 12 at the outer periphery. This permits the heart valve prosthesis to be sutured into the blood vessel such that the tissue of the blood vessel comes to lie between the stabilizing ring 14 and the suture ring 20, and the threads for suturing can be led through the suture ring 20, the body tissue lying therebetween and then through the stabilizing ring 14. Thereby, the suture material is led through the sheath surrounding the stabilizing ring 14 and through the openings 16 in the stabilizing ring 14. The stabilizing ring 14 thus forms a counter surface on suturing, so that additional felts as counter surfaces are not necessary.

Figure 6:
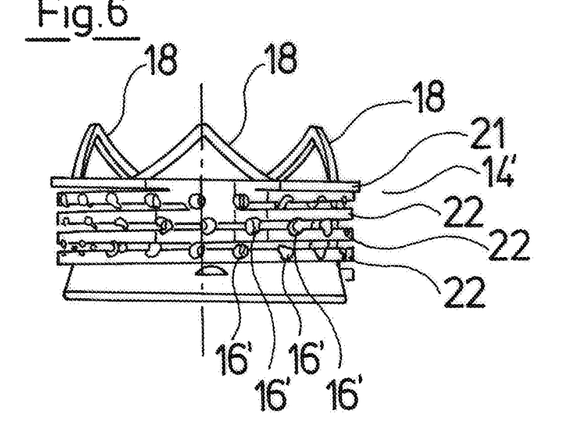
FIG. 6 is a lateral view of a stabilizing ring according to a second embodiment of the invention.
Figure 7:
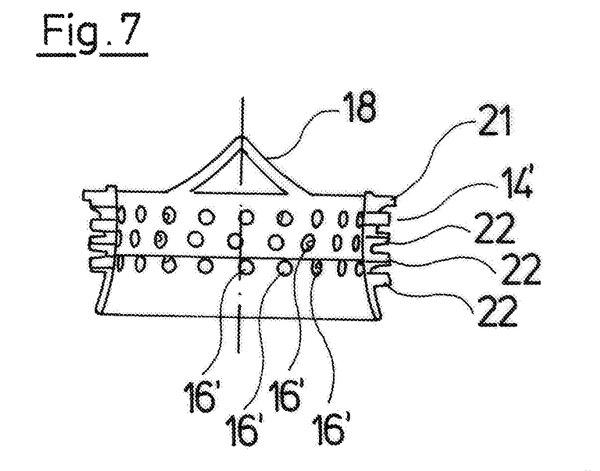
FIG. 7 is a sectioned view of the stabilizing ring according to FIG. 7.
Figure 8:
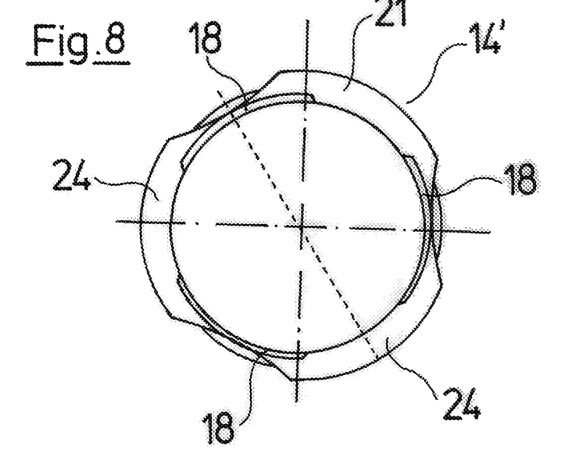
FIG. 8 is a plan view of the stabilizing ring according to FIG. 6.

An alternative stabilizing ring 14' which can be used instead of the previously described stabilizing ring 14 is shown in FIGS. 6 to 8. In contrast to the previously described stabilizing ring 14, the alternative stabilizing ring 14' comprises thread fights 22 on its outer periphery, with the help which flights the stabilizing ring 14' with the remaining parts of the heart valve prosthesis which are attached thereon can be screwed or rotated into the blood vessel. The thread flights 22 thereby engage into the body tissue and form a firm fixation of the stabilizing ring 14' and thus of the entire heart valve prosthesis in the blood vessel. The openings 16' on the stabilizing ring 14' are designed as circular through-holes which extend in the radial direction. On the one hand, these through-openings 16' can likewise serve for leading suture material through the stabilizing ring 14' for the additional fixation, and on the other hand they form undercuts on the thread flights 22, said undercuts leading to such a positive engagement between the body tissue and the thread flights 2, that the rotation movement is blocked after the insertion and a fixed engagement is achieved. A heart valve prosthesis with the stabilizing ring 14' is therefore preferably fixed in the blood vessel without additional suturing.

The remaining parts of the heart valve prosthesis with the stabilizing ring 14' can be designed in the previously described manner. The commissure supports 18 are also designed in a manner which is identical to the preceding description. At that axial end, at which the commissure supports 18 are formed and which faces the valve frame 2, the stabilizing ring 14' comprises a radially outwardly directed collar 21 which serves for fastening on the sheath 12 or fabric material connecting the stabilizing ring 14' to the valve frame 2 and to the valve leaflets 8. This means that the stabilizing ring 14' can remain unsheathed with this embodiment, so that it can engage with the body tissue in a direct manner.

Figure 9:
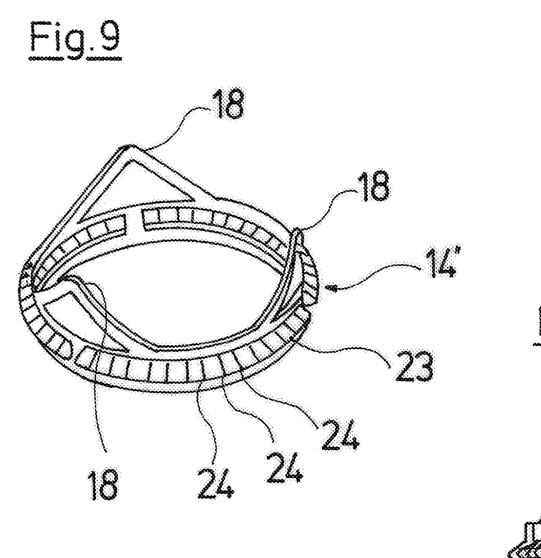
FIG. 9 is a perspective view of a stabilizing ring according to a third embodiment of the invention.
Figure 10:
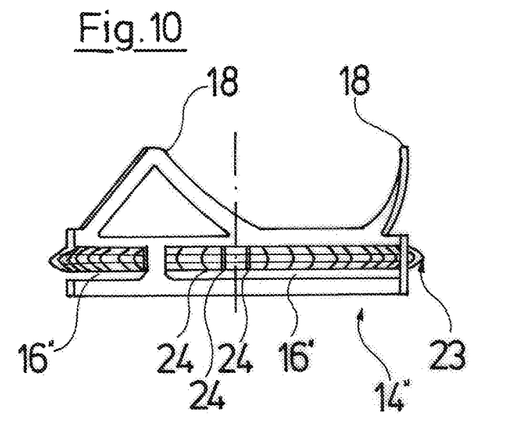
FIG. 10 is a sectioned view of the stabilizing ring according to FIG. 9.

FIGS. 9 and 10 show a third variant of the stabilizing ring 14". Instead of the thread flights 22 with the previously described embodiment, the stabilizing ring 14" of the third embodiment comprises differently designed projections or prominences 23, which project or protrude radially outwards from the stabilizing ring 14". In this embodiment example, the projections are formed by a protuberance which is v-shaped in cross section and extends essentially over the complete periphery. This protuberance comprises a multitude of indentations or notches 24, so that a multitude of projections or teeth which are v-shaped in cross section and lie next to one another are formed, wherein the tips of the projections form the radially outer-lying point in each case. This projection or these teeth can engage into the surrounding tissue for the fixation of the stabilizing ring 14". The projections with an axial end are fixedly connected to the stabilizing ring 14". An arched opening 16" is present at the opposite axial end. This opening, as described above, on the one hand can be used in order to lead suture material through the stabilizing ring 14", and on the other hand the opening 16" is preferably designed such that the projections 23 can be deformed radially inwards out of their angled shape, so that they essentially do not project outwards beyond the outer periphery of the stabilizing ring 14". An installation position, in which the stabilizing ring 14' can be inserted into the aorta, can therefore be created. After the insertion, the projections 23 can then be pivoted or deformed into the represented projecting position, in order to engage with the surrounding tissue, for the fixation of the stabilizing ring 14'. This can be effected for example by way of mechanical pressure from the inside, for example with the help of a balloon or by way of using a shape memory material. If a shape memory material such a nitinol is used, then the projections 23 can be deformed back into the rest position shown in FIGS. 9 and 10 by way of heating. The preceding description of the first two embodiments is referred to with regard to the remaining designs of the stabilizing ring in FIGS. 9 and 10.

Figure 11:
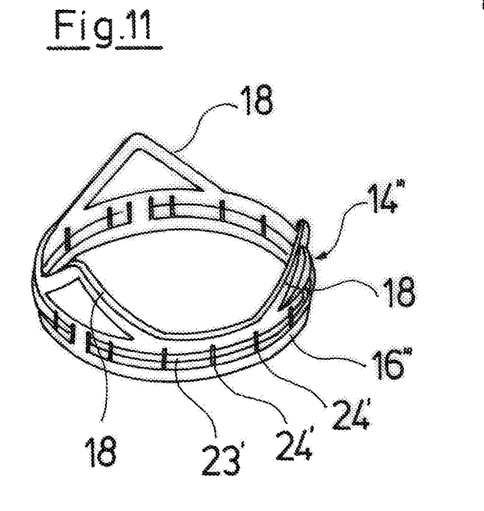
FIG. 11 is a perspective view of a stabilizing ring according to a fourth embodiment of the invention.
Figure 12:
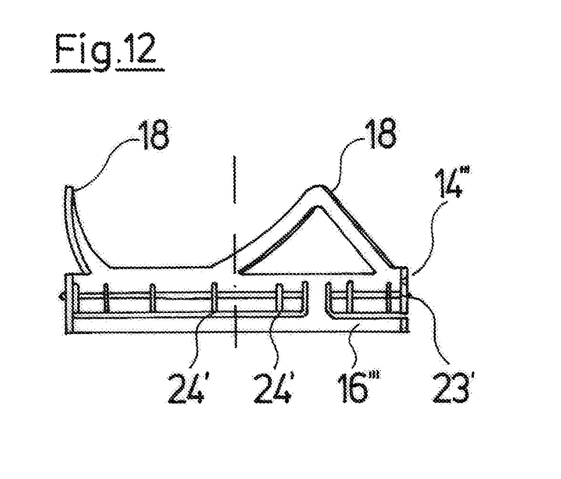
FIG. 12 is a sectioned view of the stabilizing ring according to FIG. 11.

The stabilizing ring 14''' shown in the FIGS. 11 and 12 differs from the design according to FIGS. 9 and 10 in that the radially outwardly directed, peripheral protuberance which forms the projections 23 is designed smaller in cross section, and the indentations 24' are distanced further. The individual elements, teeth or projections 23' are thus larger, wherein the radial projections are designed shorter in the radial direction. The function otherwise corresponds to that of the preceding description. The opening 16' can also be used for the same purpose as the previously described opening 16". The preceding description of the first three embodiments is referred to concerning the remaining design of the stabilizing ring 14'''.

Figure 13:
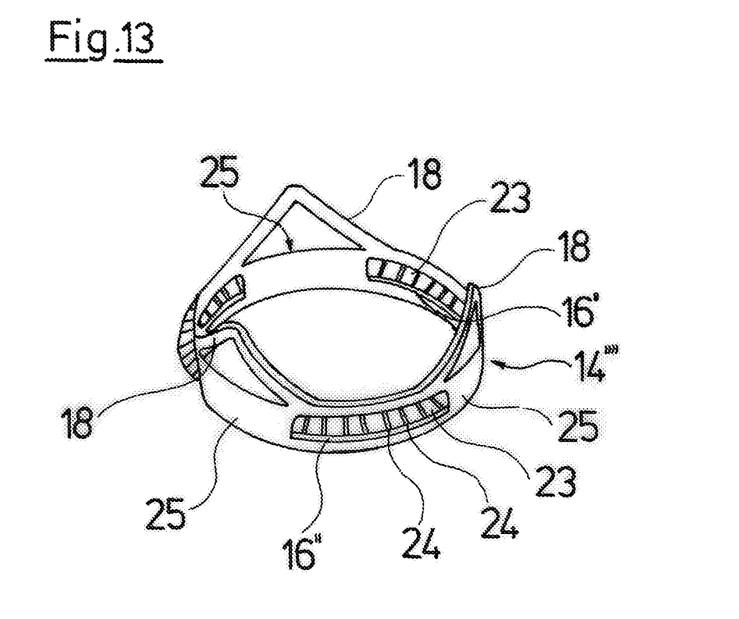
FIG. 13 is a perspective view of a stabilizing ring according to a fifth embodiment of the invention.
Figure 14:
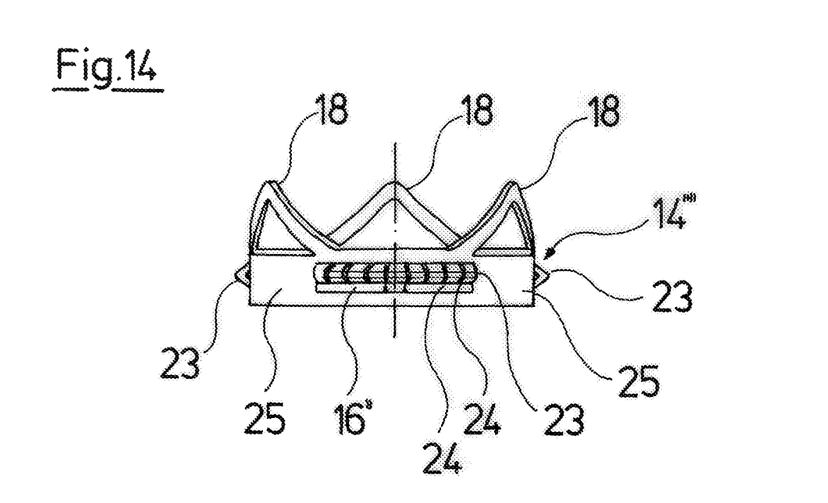
FIG. 14 is a lateral view of the stabilizing ring according to FIG. 13.

FIGS. 13 and 14 show a stabilizing ring 14'''' which represents a variant of the embodiment of FIGS. 9 and 10, and the difference in the design of the stabilizing ring 14'''' to the design of the stabilizing ring 14" lies in the peripheral sections 25 of the stabilizing ring 14''' which are situated in the region of the commissure supports 28 being free of projections 23. The outer peripheral sections 25 of the stabilizing ring 14'''' are the peripheral regions which bear on the interleaflet triangles in the aorta in the installed condition of the heart valve prosthesis. These regions are free of projections 23, in order to avoid injury to the tissue in these regions. Concerning the embodiment in FIGS. 13 and 14, it is to be understood that the previously described embodiments of the stabilizing ring according to FIGS. 6-12 can also be designed in a manner such that the peripheral sections 25 are free of projections in the region of the commissure supports 18 lying opposite the leaflet triangles on installation.

Otherwise, with regard to all embodiments according to FIGS. 6-14, it is to be understood that the fastening in the tissue with the help of projections for assisting or replacing the suturing (sutureless fastening), which is described there, can also be applied with other heart valve prosthesis, in particular mechanical heart valve prostheses.

A special form of the valve leaflets for the heart valve prosthesis shown in FIGS. 1-5 is now described hereinafter by way of FIGS. 15-17. This shape of the valve leaflets could also be applied independently of the use of a fastening or stabilizing ring 14, 14', 14", 14''' and 14''''.

Figure 15:
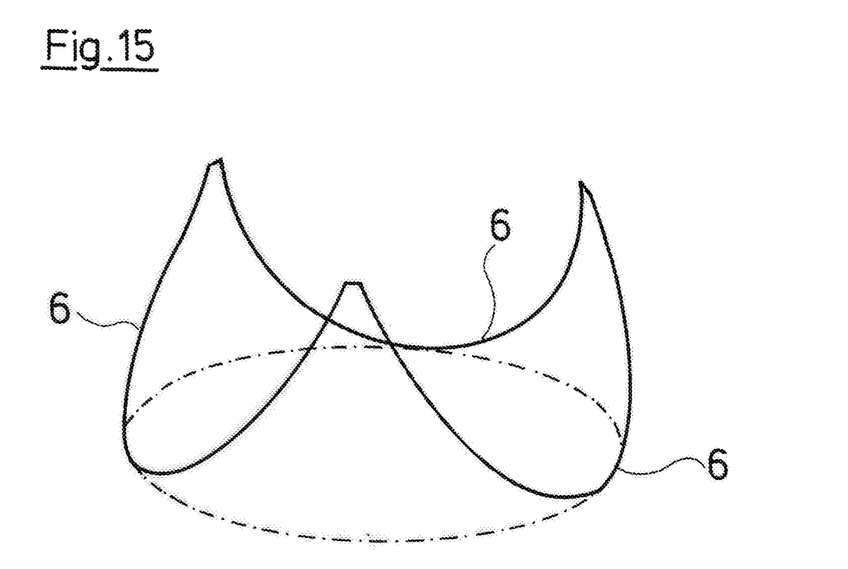
FIG. 15 is a perspective representation of the attachment edge for the valve leaflets.

FIG. 15 schematically shows the three arches 6 of the valve frame which simultaneously define the attachment edge of the valve leaflets 8. The valve leaflets 8 preferably have a shape as is shown in FIG. 16, when they are spread out in a flat manner. A first region of the outer contour forms the free face edges which define the contact edges 10, with which the valve leaflet 8 comes to bear in a sealing manner on the two other valve leaflets. A second region of the outer contour forms the attachment edge on an arch 6 of the valve frame 2. This attachment edge is formed from five circular sections which are to say arcs. The two outer arcs 26 which are adjacent to the contact edges 10 have the same radius of curvature, in each case of a circle or arc b1. These two arcs 26 are bent outwards, which is to say the middle points of the circles b1 lie outside the surface of the valve leaflet 8. The valve leaflet 8 therefore has a shape which increasingly widens to the contact edges 10 in the region of the outer arcs 26. First inner arcs 28 which are likewise identically curved and have a radius of curvature which corresponds in each case to a second circle b2 connect inwardly onto the outer arcs 26. The radius of curvature of the second circles b2 is smaller than the radius of curvature of the circle b1. The first inner arcs 28 are inwardly curved. This means that the middle points, about which the two arcs 28 are curved, lie within the contour of the valve leaflet 8. A second inner arc 30 which is likewise inwardly curved and has a radius of curvature which corresponds to a third circle b3 is situated between the two first inner arcs 28, wherein this third circle b3 has radius which is larger than the radius of the circles b2 and smaller than the radius of the circles b1.

The valve leaflet 8 as a whole is formed symmetrically to a middle line M, wherein the middle point of the circle b3 lies on this middle line. The middle line M moreover extends through the middle of the second inner arc 30. The contact point of the two contact edges 10 moreover lies on this middle line or symmetry line M. Departing from the intersection point of the middle line M with the second inner arc 30, the outer contour of the valve leaflet 8 which defines the attachment line on the arch 6 thus firstly has an increasing, inwardly directed curvature in the transition from the second inner arc 30 to the first inner arc 28, in order to then merge into an outwardly directed lower curvature, in the transition from the first, inner arc 28 to the outer arc 26.

On account of this design of the valve leaflets, one succeeds in the valve leaflets being able to open such that as a whole they essentially define sections of the outer peripheral surface of a circular cylinder which is to say release a circular opening of a maximally large cross section. This is explained by way of FIG. 17. There, three attachment points A1, A2, A3 and accordingly attachment points B1, B2 and B3 lying opposite these in the planes E1, E2 and E3 are considered by way of example. Thereby, the attachment point B1 is mirror-symmetrical to the attachment point A1, the attachment point B2 is mirror-symmetrical to the attachment point A2 and the attachment point B3 is mirror symmetrical to the attachment point A3, with respect to the line of symmetry S of the arch 6. If the valve leaflet 8 is in its opened position, then all three connecting lines, which is to say the connecting line between the attachment points A1 and B1, the connecting line between the attachment points A2 and B2 and the connecting line between the attachment points A3 and B3 lie on the same arc L1 which defines the circular opening. This would also be the case for all other lines normal to the symmetry line S between the two sides of the arch 6, which is to say between two opposite attachment points. The valve leaflet 8 in the opened condition can thus move into the shape of a peripheral section a circular cylinder with the cross section of the arc L1 and thus ensure a maximal opening. In contrast to this, the opening line L2 of conventional valve leaflets resulting from the length of the valve flap between the attachment points A1 and B1 not being sufficiently long, is shown in FIG. 17 in a schematically dashed manner.

Figure 16:
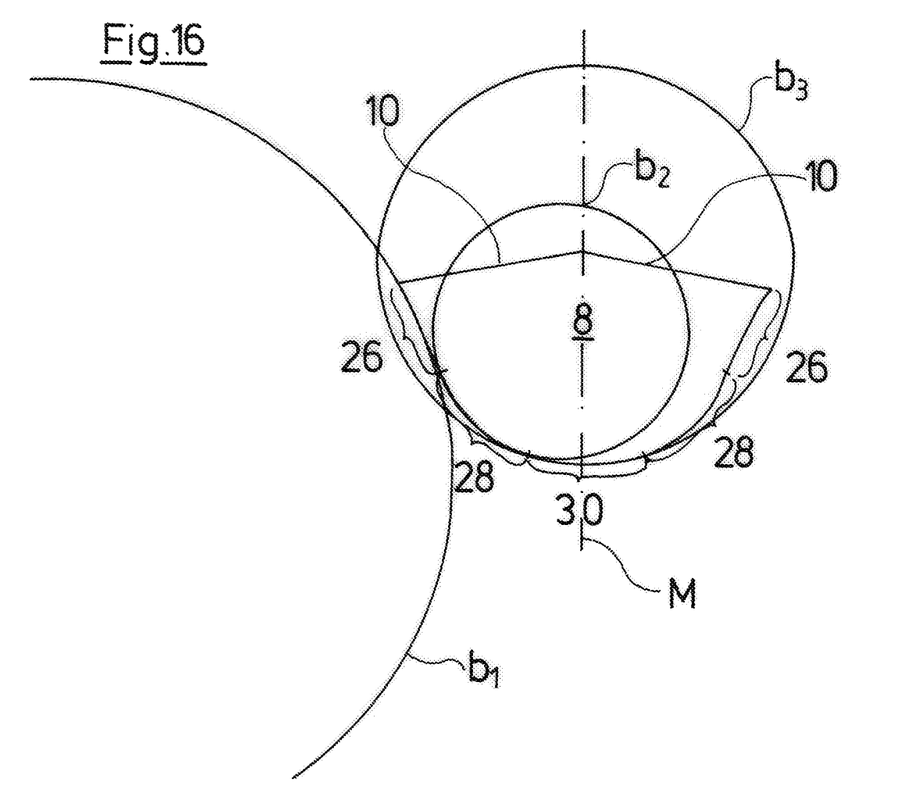
FIG. 16 is a view showing a design of the outer edge of a valve leaflet.
Figure 17:
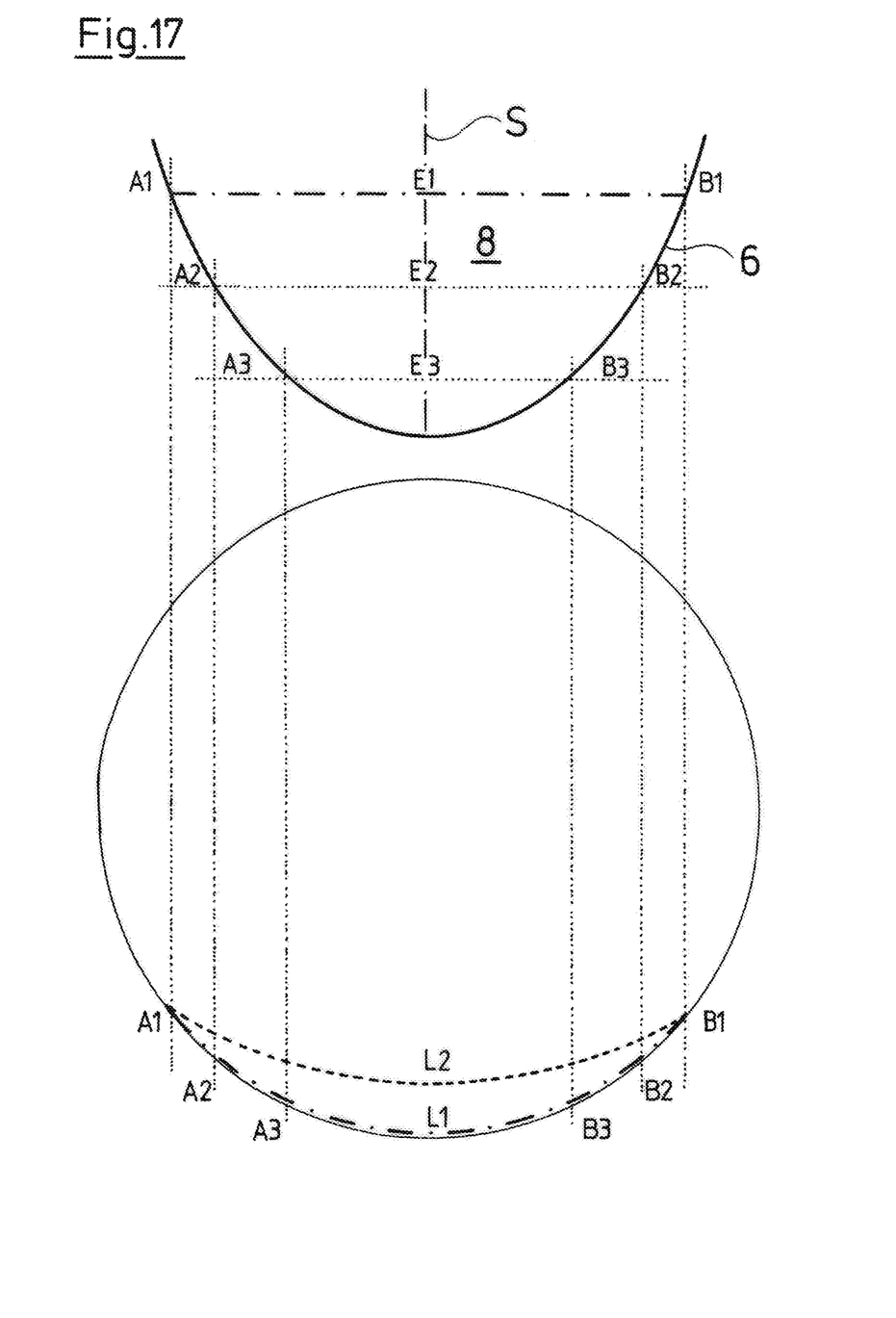
FIG. 17 is a schematic representation of the attachment points and length (leaflet width) of a valve leaflet, given a maximum opening.

It is to be understood that the design of the valve leaflets 8, as has been explained by way of FIGS. 15 to 17, can also be used independently of the use of the stabilizing ring 14, 14', 14', 14''' and 14'''' as has been described previously.

While specific embodiments of the invention have been shown and described in detail to illustrate the application of the principles of the invention, it will be understood that the invention may be embodied otherwise without departing from such principles.

The invention claimed is:

1. A heart valve prosthesis comprising:
a valve frame comprises commissures with a plurality of lower arcuate portions;
a plurality of valve leaflets fastened on the valve frame;
a fastening region which connects axially onto the valve frame, for fastening in a blood vessel, wherein the fastening region comprises a stabilizing ring which defines a predefined shape and a predefined diameter of the fastening region and the stabilizing ring is connected to the valve frame in a force-decoupled movable manner via a flexible connection, wherein at least one of the lower arcuate portions of the valve frame extends radially beyond an outer periphery of the stabilizing ring when the valve frame is in a non-deformed state.

2. A heart valve prosthesis according to claim 1, wherein the valve leaflets are manufactured of biological material.

3. A heart valve prosthesis according to claim 1, wherein the valve frame is elastically deformable.

4. A heart valve prosthesis according to claim 1, wherein the stabilizing ring is connected to the valve frame via the flexible connection such that the valve frame is movable relative to the stabilizing ring.

5. A heart valve prosthesis according to claim 1, wherein the stabilizing ring is connected to the valve frame only via a fabric material, wherein the fabric material envelops the valve frame or envelopes the stabilizing ring or envelopes both the valve frame and envelopes the stabilizing ring.

6. A heart valve prosthesis according to claim 1, wherein the stabilizing ring, at least in a radial direction, has a lower elastic deformability than the valve frame and is rigid.

7. A heart valve prosthesis according to claim 1, where in the stabilizing ring is comprised of a metal shape memory alloy.

8. A heart valve prosthesis according to claim 1, wherein the stabilizing ring comprises commissure supports which project in an axial direction, are fixedly connected to the stabilizing ring and extend into commissures formed by the valve frame.

9. A heart valve prosthesis according to claim 1, wherein the stabilizing ring defines an inner cross section which corresponds to an inner cross section which is delimited by commissures of the valve frame.

10. A heart valve prosthesis according to claim 1, wherein the valve frame is elastically deformable in a radial direction.

11. A heart valve prosthesis according to claim 1, wherein the valve frame in a relaxed condition has a larger outer cross section than the stabilizing ring.

12. A heart valve prosthesis according to claim 1, wherein the stabilizing ring has an inner cross section which is configured to correspond to a cross section of a natural blood vessel for which blood vessel the heart valve prosthesis is dimensioned.

13. A heart valve prosthesis according to claim 1, wherein the stabilizing ring is provided with projections on an outer periphery thereof, said projections being provided for engaging into surrounding tissue and having a thread configuration.

14. A heart valve prosthesis according to claim 1, wherein the stabilizing ring is provided with radial openings.

15. A heart valve prosthesis according to claim 1, further comprising a flexible suture ring which, at least in sections, overlaps the stabilizing ring at an outer periphery thereof.

16. A heart valve prosthesis according to claim 1, wherein the valve leaflets have such a shape that in an opened condition the valve leaflets define sections of peripheral surfaces of a cylinder.

17. A heart valve prosthesis according to claim 16, wherein the valve leaflets each have an outer contour which is adjacent to the valve leaflet and which is composed of at least three arcs, wherein two outer arcs of the outer contour are curved outwards and one or more inner arcs situated between these outer arcs are curved inwards.

18. A heart valve prosthesis according to claim 1, wherein the valve frame is movable relative to the stabilizing ring.

* * * * *